United States Patent [19]

Motoki et al.

[11] Patent Number: 5,156,956

[45] Date of Patent: Oct. 20, 1992

[54] TRANSGULTAMINASE

[75] Inventors: Masao Motoki; Atsushi Okiyama; Masahiko Nonaka; Haruo Tanaka; Ryosuke Uchio, all of Kawasaki; Akira Matsuura, Kasugai; Hiroyasu Ando, Konan; Koichi Umeda, Gifu, all of Japan

[73] Assignees: Ajinomoto Co., Inc., Tokyo; Amano Pharmaceutical Co., Ltd., Nagoya, both of Japan

[21] Appl. No.: 726,722

[22] Filed: Jul. 1, 1991

Related U.S. Application Data

[63] Continuation of Ser. No. 162,988, Mar. 2, 1988, abandoned.

[30] Foreign Application Priority Data

Mar. 4, 1987 [JP] Japan .................. 62-049157
Jul. 1, 1987 [JP] Japan .................. 62-165067

[51] Int. Cl.$^5$ .................. C12N 9/10; C12P 21/00
[52] U.S. Cl. .................. 435/68.1; 435/193; 426/573
[58] Field of Search .................. 435/193, 68.1; 426/573

[56] References Cited

PUBLICATIONS

Juprelle-Soret M. et al, (1984) Eur. J. Cell Biol. 34, 271–274.
Icekson, I., et al. (1987) Plant Physiol 84, 972–974.
Harding, H. W. J. et al. (1972) Biochemistry 11, 2858–2863.
Plant Physiol., vol. 87, 1988, pp. 757–761; Serafini–Fracassini et al: First evidence for polyamine conjugation mediated by an enzymic activity in plants.
Agric. Biol. Chem., vol. 48, No. 5, 1984, pp. 1257–1261; Motoki et al: Functional properties of food proteins polymerized by transqlutaminase.

*Primary Examiner*—Charles L. Patterson, Jr.
*Attorney, Agent, or Firm*—Oblon, Spivak, McClelland, Maier & Neustadt

[57] ABSTRACT

A transglutaminase catalyzing an acyl transfer reaction of a γ-carboxyamide group of a glutamine residue in a peptide or protein chain in the absence of $Ca^{2+}$.

6 Claims, 6 Drawing Sheets

TRANSGULTAMINASE

This application is a continuation of application Ser. No. 07/162,988, filed on Mar. 2, 1988, now abandoned.

BACKGROUND OF THE INVENTION

1. Field of the Invention

The present invention relates to a novel transglutaminase and a process for producing a protein gelation product using the transglutaminase.

2. Description of the Background

Transglutaminases are enzymes which catalyse an acyl transfer reaction of a γ-carboxyamide group of a glutamine residue in a peptide chain.

The transglutaminases form intramolecular or intermolecular ε-(γ-Glu)-Lys cross-linking wherein the ε-amino group of the lysine residue in the protein serves as the acyl receptor. When water functions as the acyl receptor, the transglutaminases catalyze deamination of glutamine residues to form glutamic acid residues.

The gelation products of the present invention produced utilizing the novel transglutaminases are used as yoghurt, jelly, cheese, gel cosmetics, etc., including conventional gel foodstuffs and gel cosmetics. Furthermore, the gelation products in accordance with the present invention can be produced in a non-heated state and are thermally stable and therefore, can also be used over a wide range, such as raw materials for microcapsules, carriers for immobilized enzymes, etc.

Transglutaminases hitherto known are those derived from animals. Transglutaminases are widely distributed in, for example, liver of the guinea pig [Connellan, et al., Journal of Biological Chemistry, vol. 246, No. 4, pages 1093-1098 (1971)] and mammal organs and blood [Folk et al., Advances in Enzymology, vol. 38, pages 109-191 (1973) and Folk et al., Advances in Protein Chemistry, vol. 31, pages 1-133 (1977)] and, characteristics of the enzymes have been investigated.

Up to now, however, no report has been made on any transglutaminase derived from microorganisms. With respect to a process for producing gel products of protein using an animal-derived transglutaminase, the present inventors have already made investigations resulting in Published Unexamined Japanese Patent Application No. 149645/83.

However, application of the animal-derived transglutaminase to industry, particularly, the process for producing protein gelation products involves defects as described below.

It is difficult to obtain animal-derived transglutaminases at low cost and in large quantities. Also, there is the restriction that at least 1 unit of this expensive enzyme per 1 g of substrate protein and at least 2.0 wt. % of a substrate protein concentration are required for gelation. Further, the animal-derived transglutaminase is calcium ($Ca^{2+}$)dependent so that its application is limited.

Because of the foregoing defects, processes for producing gelation products using animal-derived transglutaminases are impractical.

BRIEF DESCRIPTION OF THE DRAWINGS

A more complete appreciation of the invention and many of the attendant advantages thereof will be readily obtained as the invention becomes better understood by reference to the following detailed description when considered in connection with the accompanying drawing, wherein.

Figure 1:
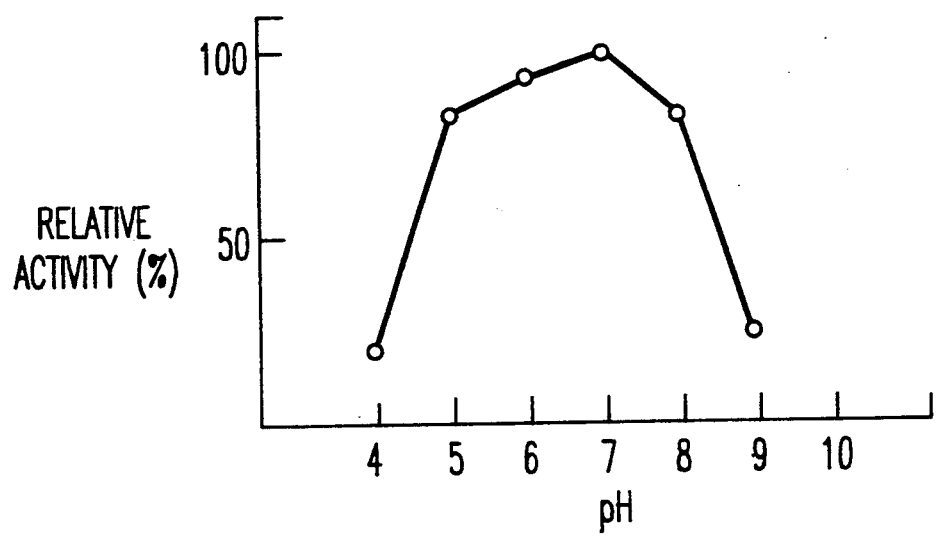
FIGS. 1, 2, 3 and 4 show an optimum pH curve, optimum temperature curve, pH stability curve and temperature stability curve of BTG-1 of the present invention, respectively.

In view of the above difficulties of applying animal-derived transglutaminases in an industrial setting, there remains a need for new and more economically obtained and used transglutaminases.

SUMMARY OF THE INVENTION

Accordingly, an object of the present invention is to provide a new transglutaminase which is free from problems such as quantity of supply, cost/performance, and ease of purification.

It is another object of the present invention to provide a transglutaminase which has great practicality since no calcium is required for the reaction catalyzed by the transglutaminase.

The present invention is further directed to a method for producing a protein gelation product by using a transglutaminase.

The above and other objects which will become more readily apparent hereinafter, have been achieved by the discovery of a novel transglutaminase derived from microorganisms.

DETAILED DESCRIPTION OF THE INVENTION

Animal-derived enzymes have been investigated heretofore but due to lack of practicability, the present inventors have made wide-ranging investigations, searching for a microorganism-derived transglutaminase. As a result, it has been found that bacteria belonging to the genus Streptoverticillium are capable of producing novel transglutaminases which catalyze an acyl transfer reaction of the γ-carboxyamide group of a glutamine residue in a peptide chain in the absence or even in the presence of $Ca^{2+}$. It has also been found that using this enzyme, protein gelation products can be produced by gelling a protein-containing solution or slurry having a protein concentration of at least 1.0 wt. %.

Specific examples of the bacteria belonging to the genus Streptoverticillium include *Streptoverticillium griseocarneum* IFO 12776, *Streptoverticillium cinnamoneum* sub sp. cinnamoneum IFO 12852, *Streptoverticillium mobaraense* IFO 13819, etc.

Methods for culture, purification, etc., which comprise culturing these microorganisms and harvesting transglutaminase (hereafter referred to as BTGase) will be described below. For the purposes of the present invention, any culturing mode of liquid culture and solid culture can be performed, but from an industrial standpoint, it is advantageous to perform deep aerial spinner culture. As culture sources to be used, there can be used carbon sources, nitrogen sources, inorganic salts and other trace nutrient sources conventionally used for culture of microorganisms; in addition thereto, all nutrient sources can be employed as long as they are utilizable by microorganisms belonging to the genus Streptoverticillium. As the carbon sources for media, there can be used, singly or in combination, glucose, sucrose, rastagen, glycerin, dextrin, starch, etc. and in addition thereto, fatty acids, oils and fats, organic acids, etc. As the nitrogen sources, any of inorganic nitrogen sources and organic nitrogen sources can be used. As the inorganic nitrogen sources, there can be used ammonium nitrate, and other ammonium salts.

Further as the organic nitrogen sources there can be used, for example, powder of soybean, rice, sweet corn and wheat etc., bran and defatted meal, and corn steep liquor, peptone, meat extract, casein, amino acids, yeast extract, etc. As the inorganic salts and the trace nutrient sources, there can be used salts of phosphoric acid, magnesium, potassium, iron, calcium, zinc etc., and any other materials that can accelerate growth of the bacteria or production of BTGase such as vitamins, non-ionic surfactants, defoaming agents, etc., if necessary. Culture may be performed under aerobic conditions at a culture temperature within such a range that the bacteria grow to product BTGase, preferably at 25° to 35° C. A time period for the culture varies depending upon conditions but the culture may be performed until BTGase is best produced, generally for about 2 to 4 days. In the case of liquid culture, BTGase is dissolved in the culture solution and can be harvested from the culture filtrate obtained by removing solid contents from the culture solution after completion of the culture.

For purification of BTGase from the culture filtrate, any method generally used for purification of enzymes can be used.

For example, there can be used treatment methods with an organic solvent such as ethanol, acetone, isopropyl alcohol, etc.; salting out using ammonium sulfate, sodium chloride, etc., dialysis, ultrafiltration, ion exchange chromatography, adsorption chromatography, gel filtration, adsorbents, isoelectric point fractionation, etc. Further in the case where the purity of BTGase is increased by the use of these methods in suitable combination, the methods can be performed in such a combination. From the enzyme obtained by these methods, liquid or solid BTGase can be obtained by methods of ultrafiltration condensation, reverse osmosis condensation, drying under reduced pressure, freeze drying or spray drying, by adding a variety of salts, sugars, proteins, lipids, surfactants, etc., as stabilizers or without adding them.

Measurement of the activity of BTGase is carried out by performing a reaction using benzyloxycarbonyl-L-glutaminyl glycine and hydroxylamine as substrates in the absence of $Ca^{2+}$, forming an iron complex with the resulting hydroxamic acid in the presence of trichloroacetic acid, measuring absorption at 525 nm and determining the amount of hydroxamic acid by a calibration curve to calculate the activity. The BTGase activity is measured by the method described below, unless otherwise indicated.

Measurement of Activity

Reagent A
0.2M Tris-hydrochloride buffer (pH 6.0)
0.1M hydroxylamine
0.01M reductive glutathione
0.03M benzyloxycarbonyl-L-glutaminyl glycine Reagent B is made of equal volumes of 3N hydrochloric acid, 12% trichloroacetic acid and 5% $FeCl_3 \cdot 6H_2O$ (dissolved in 0.1N-HCl).

To 0.05 ml of an enzyme solution is added 0.5 ml of Reagent A and they are mixed with each other. After reacting at 37° C. for 30 minutes, Reagent B is added thereto to discontinue the reaction and form an Fe complex. Thereafter, absorbance is measured at 525 nm. As a control, absorbance is measured after reacting a previously thermally inactivated enzyme solution in a similar manner and a difference in absorbance between the control and the enzyme solution is measured. Separately, a calibration curve is prepared using L-glutamic acid γ-monohydroxamio acid instead of the enzyme solution, and the amount of hydroxamic acid produced is determined by the difference in absorbance described above. An enzyme activity which produces 1 μmol of hydroxamic acid per 1 minute is defined as 1 unit.

Figure 2:
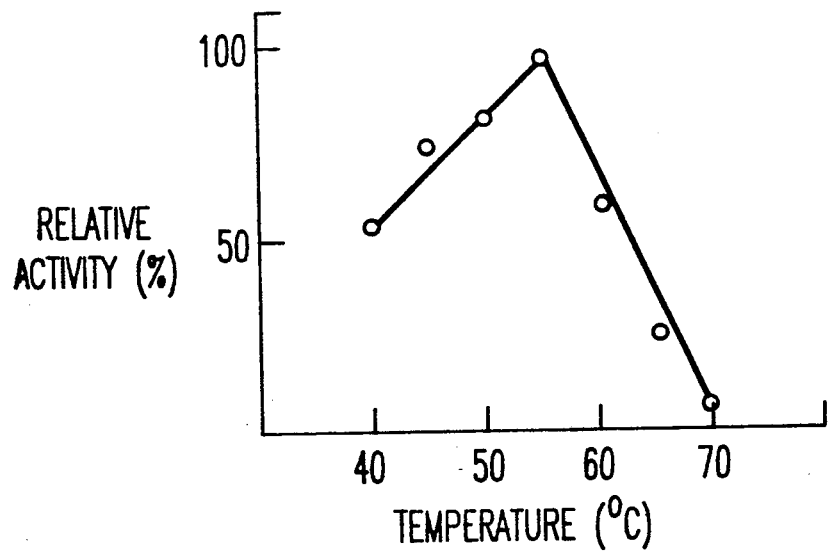
Figure 3:
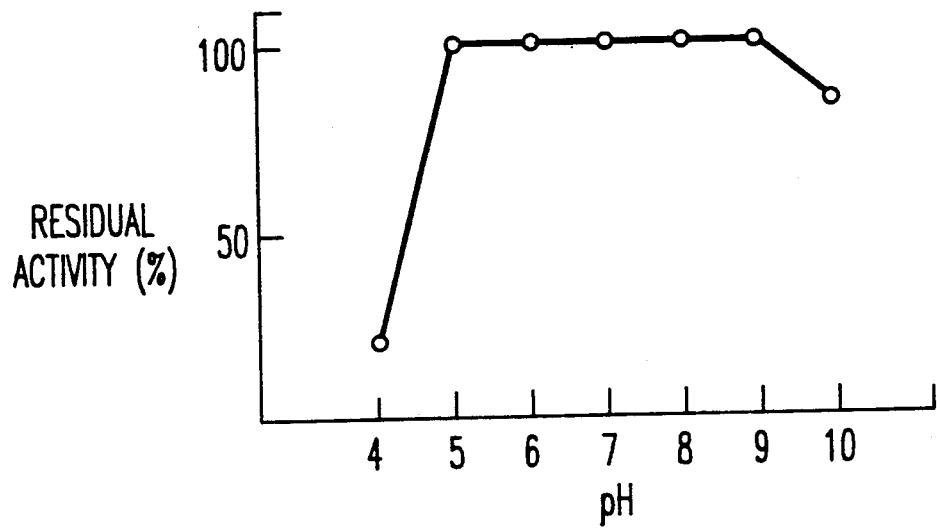
Figure 4:
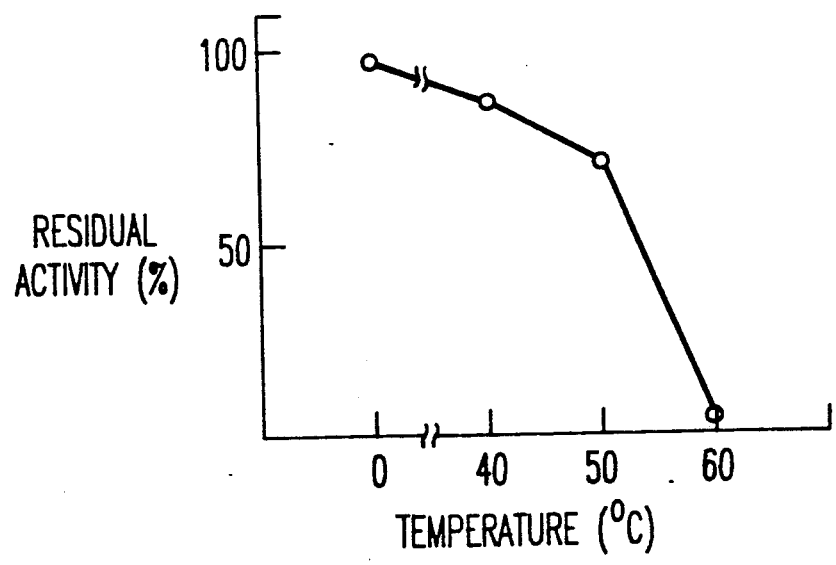
Figure 5:
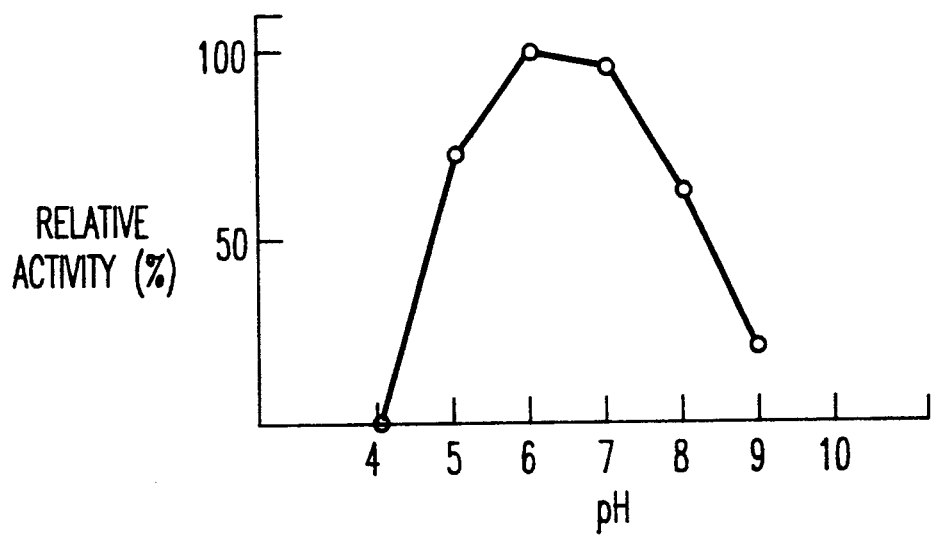
FIGS. 5, 6, 7 and 8 show an optimum pH curve, optimum temperature curve, pH stability curve and temperature stability curve of BTG-2 of the present invention, respectively.
Figure 6:
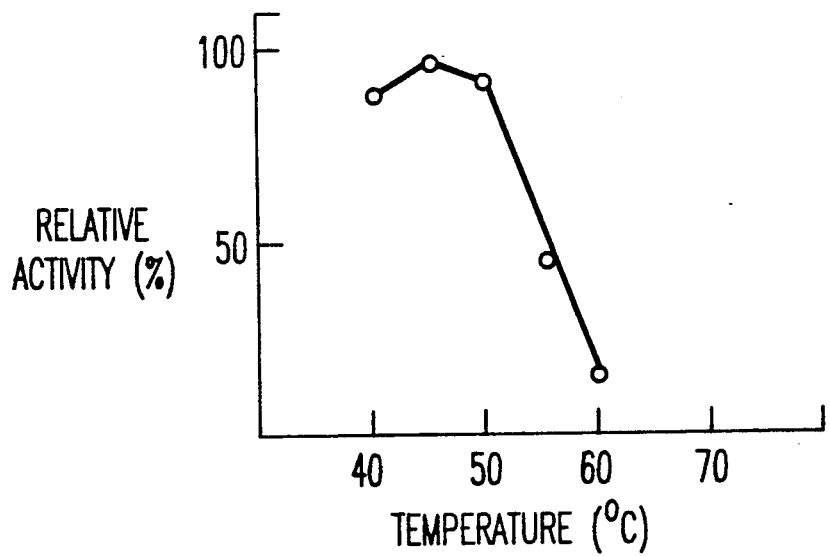
Figure 7:
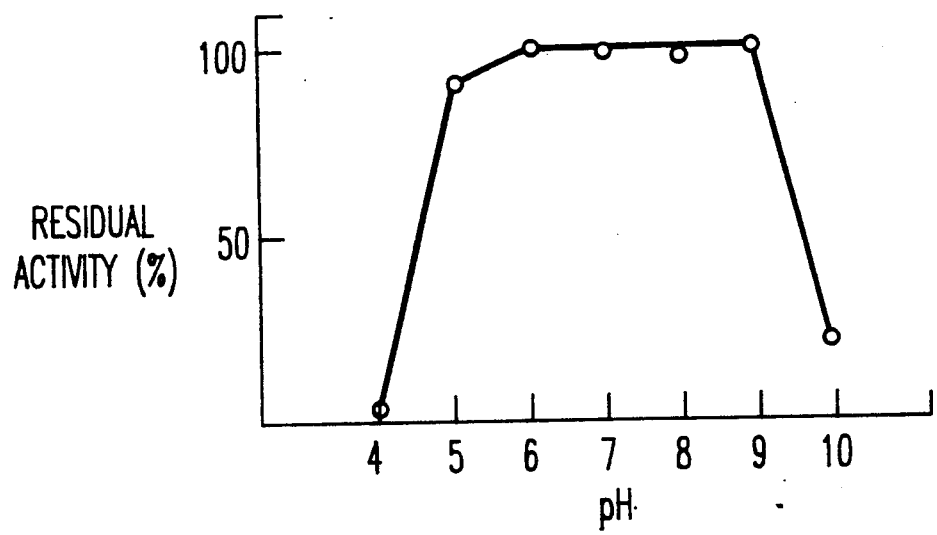
Figure 8:
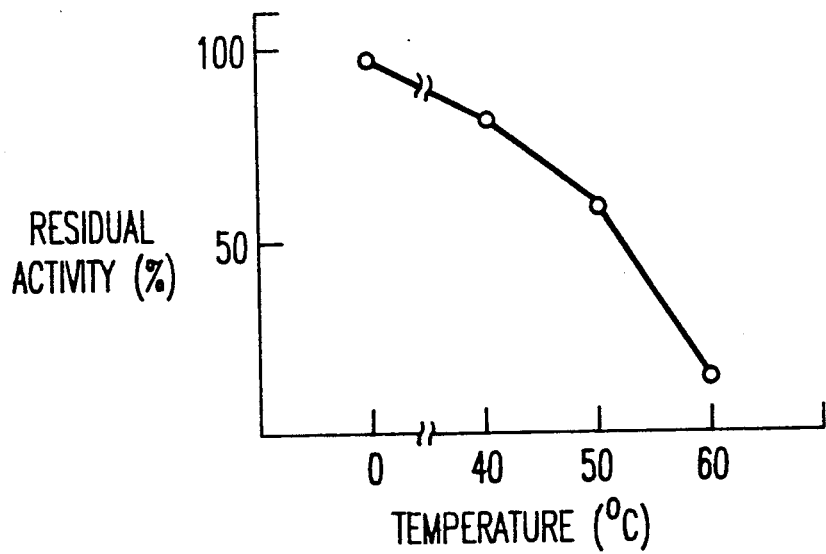
Figure 9:
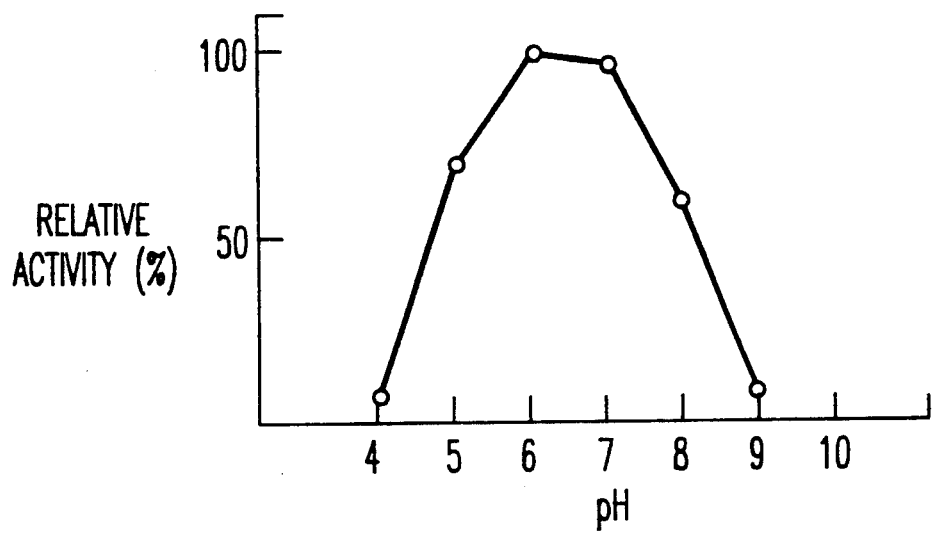
FIGS. 9, 10, 11 and 12 show an optimum pH curve, optimum temperature curve, pH stability curve and temperature stability curve of BTG-3 of the present invention, respectively.
Figure 10:
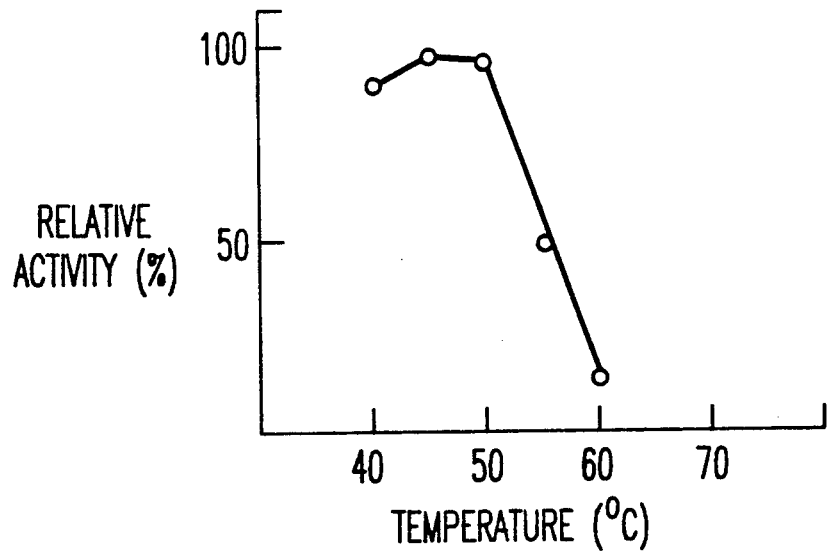
Figure 11:
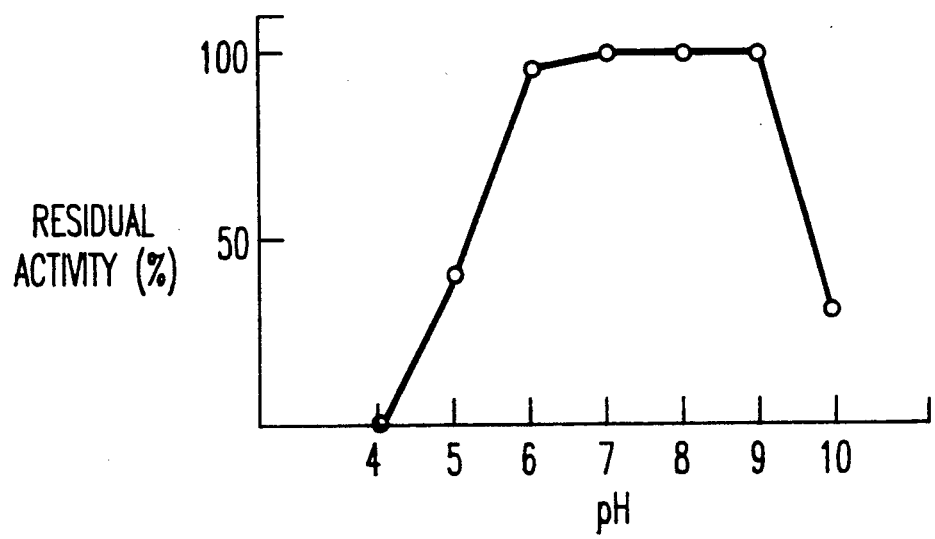
Figure 12:
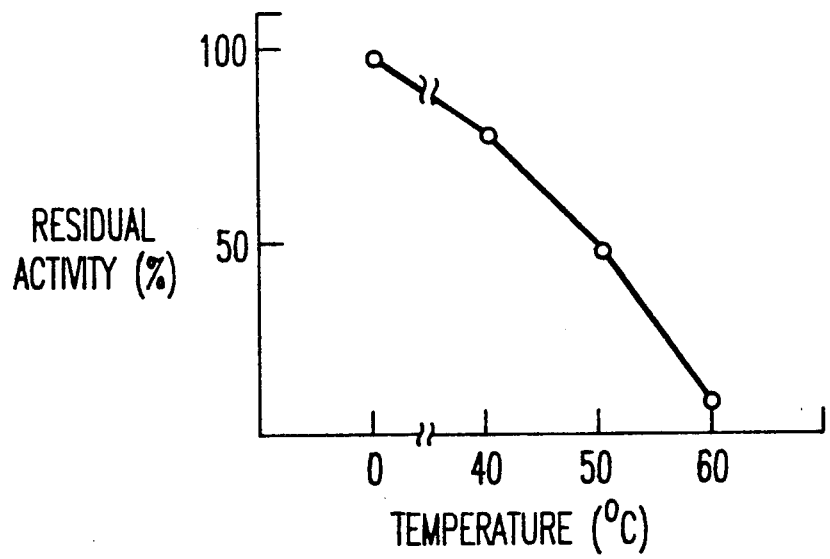

Enzymological properties of the thus obtained purified BTGases, namely, transglutaminase of *Streptoverticillium mobaraense* IFO 13819 (named BTG-1), transglutaminase of *Streptoverticillium griseocarneum* IFO 12776 (named BTG-2) and transglutaminase of *Streptoverticillium cinnamoneum* sub sp. cinnamoneum IFO 12852 (named BTG-3) are described below.

a) Optimum pH:

In the case of using benzyloxycarbonyl-L-glutaminyl glycine and hydroxylamine as substrates, the optimum pH of BTG-1 lies in a range of 6 to 7, the optimum pH of BTG-2 lies in a range of approximately 6 to 7 and the optimum pH of BTG-3 lies in a range of approximately 6 to 7, upon the reaction at 37° C. for 10 minutes (shown in FIGS. 1, 5 and 9).

b) Optimum temperature:

In the case of using benzyloxycarbonyl-L-glutaminyl glycine and hydroxylamine as substrates, the optimum temperature of BTG-1 lies at about 55° C., the optimum temperature of BTG-2 lies at about 45° C. and the optimum temperature of BTG-3 lies at about 45° C., upon the reaction at pH 6 for 10 minutes (shown in FIGS. 2, 6 and 10).

c) pH Stability:

By treatment at 37° C. for 10 minutes, BTG-1 is stable at pH of 5 to 9, BTG-2 is stable at pH of 5 to 9 and BTG-3 is stable at pH of 6 to 9 (shown in FIGS. 3, 7 and 11).

d) Temperature stability:

By treatment at pH 7 for 10 minutes, BTG-1 retains 88% activity at 40° C. and 74% at 50° C.; BTG-2 retains 86% activity at 40° C. and 56% at 50° C.; and BTG-3 retains 80% activity at 40° C. and 53% at 50° C. (shown in FIGS. 4, 8 and 12).

e) Substrate specificity:

Using each BTGase, reactions of various synthetic substrates with hydroxylamine were examined. No BTGase reacts with the synthetic substrates benzyloxycarbonylasparaginyl glycine, benzyloxycarbonyl glutamine and glycylglutaminyl glycine. However, the reactivity is the highest when the synthetic substrate is benzyloxycarbonylglutaminyl glycine. In this case, the concentration of various synthetic substrates is 5 mM. The results are shown in Table 1. In the table, CBZ, Gln, Gly and Asn are abbreviations for benzyloxycarbonyl group, glutaminyl group, glycyl group and asparaginyl group, respectively.

TABLE 1

| Substrate | BTG-1 | BTG-2 | BTG-3 |
|---|---|---|---|
| CBZ—Gln—Gly | 100 | 100 | 100 |
| CBZ—Gln—Gly—OEt | 63 | 44 | 42 |
| CBZ—Gln—Gln—Gly | 38 | 39 | 35 |
| CBZ—Gly—Gln—Gly—Gly | 8 | 12 | 11 |
| CBZ—Gly—Gly—Gln—Gly | 23 | 58 | 60 |
| CBZ—Gln | 0 | 0 | 0 |
| CBZ—Asn—Gly | 0 | 0 | 0 |
| Gly—Gln—Gly | 0 | 0 | 0 | f) Influence of metal ions:

Various metal ions were added to the activity measurement system in a concentration of 1 mM (the results are shown in Table 2). In all BTGases, the activity is inhibited by $Cu^{2+}$ and $Zn^{2+}$.

TABLE 2

| Metal Ion | BTG-1 (%) | BTG-2 (%) | BTG-3 (%) |
|---|---|---|---|
| None | 100 | 100 | 100 |
| $CaCl_2$ | 101 | 102 | 102 |
| $BaCl_2$ | 101 | 99 | 105 |
| $CoCl_2$ | 103 | 103 | 103 |
| $CuCl_2$ | 79 | 82 | 86 |
| $FeCl_3$ | 96 | 104 | 106 |
| KCl | 96 | 99 | 105 |
| $MgCl_2$ | 102 | 104 | 103 |
| $MnCl_2$ | 98 | 97 | 97 |
| NaCl | 99 | 102 | 101 |
| $NiCl_2$ | 102 | 100 | 101 |
| $Pb(CH_3COO)_2$ | 97 | 97 | 100 |
| $SrCl_2$ | 100 | 101 | 100 |
| $ZnCl_2$ | 15 | 24 | 24 | g) Influence of inhibitor:

Each inhibitor was added to a concentration of 1 mM. After allowing the mixture to stand at 25° C. for 30 minutes, the activity was measured (the results are shown in Table 3). In all BTGases, the activity is inhibited by p-chloromercury benzoic acid (simply referred to as PCMB), N-ethylmaleimide (simply referred to as NEM) and, monoidoacetic acid.

TABLE 3

| Inhibitor | BTG-1 (%) | BTG-2 (%) | BTG-3 (%) |
|---|---|---|---|
| None | 100 | 100 | 100 |
| EDTA | 102 | 98 | 99 |
| PCMB | 54 | 61 | 63 |
| NEM | 5 | 5 | 3 |
| Monoiodoacetic acid | 64 | 50 | 67 |
| PMSF | 104 | 95 | 101 |

In Table 3, PMSF is the abbreviation for phenylmethylsulfonyl fluoride.

h) Isoelectric point:

According to ampholine isoelectric point electrophoresis, isoelectric points, pI, of BTG-1, pI of BTG-2 and pI of BTG-3 are approximately 9, 9.7 and 9.8, respectively.

i) Molecular weight:

According to SDS disc electrophoresis, molecular weights of BTG-1, BTG-2 and BTG-3 are approximately 38,000, 41,000 and 41,000, respectively.

Next, properties of BTGases are compared to those of guinea pig liver-derived transglutaminase. The guinea pig liver-derived transglutaminase was prepared by the method described in Published Unexamined Japanese Patent Application No. 149645/83. In Table 4, comparison in enzymological properties is shown and influence of $Ca^{2+}$ on activity is shown in Table 5. As will be apparent from Tables 4 and 5, various differences in enzymological properties are noted between transglutaminase of guinea pig liver (hereafter referred to as MTGase) which has been mainly investigated heretofore and BTGases derived from actinomycetes; in particular, differences are noted in temperature stability, molecular weight, isoelectric point and substrate specificity. Further, a difference is noted in that the BTGases of the present invention act in the presence and absence of $Ca^{2+}$. Therefore, the respective enzymes of the present invention are different from MTGase in their properties.

TABLE 4

| | BTG-1 | BTG-2 | BTG-3 | MTGase |
|---|---|---|---|---|
| Optimum pH | 6-7 | 6-7 | 6-7 | 6 |
| pH Stability | 5-9 | 5-9 | 6-9 | 6-7.5 |
| Optimum temperature | ca. 55° C. | ca. 45° C. | ca. 45° C. | 50-55° C. |
| Temperature stability (%) | | | | |
| 40° C. residual rate | 88 | 86 | 80 | 96 |
| 50° C. residual rate | 74 | 56 | 53 | 40 |
| Molecular weight | ca. 38,000 | ca. 41,000 | ca. 41,000 | ca. 90,000 |
| Isoelectric point | 9.0 | 9.7 | 9.8 | 4.5 |
| Substrate specificity (%) | | | | |
| CBZ—Gln—Gly | 100 | 100 | 100 | 100 |
| CBZ—Gln—Gly—OEt | 63 | 44 | 42 | 122 |
| CBZ—Gln—Gln—Gly | 38 | 39 | 35 | 288 |
| CBZ—Gly—Gln—Gly—Gly | 8 | 12 | 11 | 126 |
| CBZ—Gly—Gly—Gln—Gly | 23 | 58 | 60 | 27 |

TABLE 5

| Metal Ion | BTG-1 (%) | BTG-2 (%) | BTG-3 (%) | MTGase (%) |
|---|---|---|---|---|
| None | 99 | 98 | 100 | 0 |
| 1 mM $CaCl_2$ | 100 | 100 | 99 | 39 |
| 5 mM $CaCl_2$ | 100 | 100 | 98 | 100 |

Next, the process for producing protein gelation products using BTGases will be described below.

First, the protein as substrate is not limited to its origin and properties but can be vegetable protein, animal protein, microorganism protein, alga protein, etc., as far as it contains lysine residues and glutamine residues and is acted upon by the aforesaid enzymes. The kind of vegetable protein is not particularly limited but there may be mentioned, for example, defatted products of oil crop seeds and protein separated therefrom. The kind of animal protein is not particularly limited but there may be mentioned, for example, milk protein, gelatin, collagen, serum albumin, etc.

Further, as the protein used in the present invention, protein partially cleaved by a protease, etc., synthetic peptides and various proteins chemically modified can be used as the substrate of the enzyme, in addition to those described above, as long as the requirements for the glutamine residue and lysine residue being possessed are met.

In the case of a liquid or slurry of 1 wt. % or more of these proteins, preferably 3 wt. % or more, highly viscous products or gelation products are formed by the addition of BTGase; when the amount is 1 wt. % or less, solution-like or precipitate-like cross-linked high molecular weight compounds are obtained. BTGase is incorporated in an amount of 0.01 to 2000 units, preferably 0.1 to 200 units or more, based on 1 g of the protein. The pH of the reaction solution is adjusted to 4 to 10, preferably 5 to 8. Incubation at 5° to 80° C., preferably 40° to 60° C. for 10 seconds to 24 hours, preferably 10 minutes to 2 hours, gives cross-linked high molecular weight compounds or gelation products. As described above, BTGases of the present invention are novel enzymes having characteristics that they can cause gelation in a low enzyme content (0.01 unit may be sufficient per 1 g of the substrate protein), and can be used in a low substrate concentration (1 wt. % may be sufficient), etc.

By the treatment of BTGases, sufficiently gelled products can be obtained but if necessary, the gelation products after completion of the reaction can also be thermally treated at 60° to 200° C. for 1 minute to 24 hours to give further strongly gelled products. The protein-containing solution is not limited simply to a mixture of protein and water but may be any of oil-in-water type or water-in-oil emulsion by mixing protein, water and oils and fats. Various salts, starch, oligosaccharides, polysaccharides, flavors, moisturizing agents, coloring agents, etc., can also be appropriately chosen and incorporated therein within such a range that does not inhibit the conversion into high molecular weight compounds and gelation by BTGases.

By choosing the kind and amount of protein, the degree of cross-linking of the cross-linked high molecular weight compounds can be varied, whereby physical properties and moisture content of the formed gel can be varied depending upon purpose and utility.

The invention now being generally described, the same will be better understood by reference to certain examples which are included herein for purposes of illustration only and are not to be considered to be limiting thereof.

EXAMPLES

Example 1

*Streptoverticillium mobaraense* IFO 13819 was inoculated on 200 ml of medium (pH 7) having a medium composition of 0.2% of polypeptone, 0.5% of glucose, 0.2% of dipotassium phosphate and 0.1% of magnesium sulfate followed by culturing at 30° C. for 48 hours. The obtained seed culture solution was added to 20 l (pH 7) composed of 2.0% of polypeptone, 2.0% of soluble starch "Rastagen" (trademark, manufactured by Nichiden Kagaku K.K.), 0.2% of dipotassium phosphate, 0.1% of magnesium sulfate, 0.2% of yeast extract and 0.05% of defoaming and antifoaming polyoxyalkylene glycol "Adekanol" (trademark, manufactured by Asahi Denka Kogyo K.K.) followed by culturing at 30° C. for 3 days. After filtering, 18.5 l of the culture solution was obtained. The activity was 0.35 U/ml.

The culture solution was adjusted with hydrochloric acid to pH of 6.5 and passed through a column of methacrylic porous cation-exchange resin "Amberlite CG-50" (trademark, manufactured by Rohm & Haas Co., Ltd.), which had been previously equilibrated with 0.05M phosphate buffer (pH 6.5). By this operation, transglutaminase was adsorbed. After washing protein impurities out with the buffer, a density gradient of 0.05 to 0.5M was prepared by the buffer, through which the system was passed. The eluate was fractionated and recovered, and fractions having a high specific activity were collected. After the system was diluted to have a conductivity of 10 ms or less, it was passed through a column of blue Sepharose. By this operation, transglutaminase was adsorbed. After washing protein impurities out with 0.05M phosphate buffer (pH 7), a density gradient of 0 to 1M was prepared by sodium chloride, through which the system was passed. The eluate was recovered and fractions having a high specific activity were collected. The fractions were condensed using a UF 6000 membrane and equilibrated with 0.05M phosphate buffer (pH 7) containing 0.5M sodium chloride.

The obtained condensate was passed through a column of Sephadex G-75 (manufactured by Pharmacia Fine Chemical Co., Ltd.) which had been previously equilibrated with the buffer and the buffer was caused to flow therethrough to fractionate the eluate. As a result, the active fraction eluted as a single peak. The specific activity was 625 times that of the culture filtrate and the recovery rate was 47%.

Example 2

*Streptoverticillium griseocarneum* IFO 12776 was cultured at 30° C. for 3 days in a manner similar to Example 1. After filtering, 19 l of the culture solution was obtained. The specific activity was 0.28 U/ml.

The enzyme was purified in a manner similar to Example 1 and a single enzyme was obtained by SDS disc electrophoresis.

Example 3

*Streptoverticillium cinnamoneum* sub sp. cinnamoneum IFO 12852 was cultured at 30° C. for 3 days in a manner similar to Example 1. After filtering, 18.5 l of the culture solution was obtained. The specific activity was 0.5 U/ml.

The enzyme was purified in a manner similar to Example 1 and a single enzyme was obtained by SDS disc electrophoresis.

Example 4

1) The BTGase (freeze dried product, specific activity of 2.50 Units/mg protein) prepared in Example 1 was added to 5 ml of each of 5 and 10 wt. % solutions or suspensions of protein foodstuffs prepared by the method described in Example 1 of Published Unexamined Japanese Patent Application No. 149645/83 or purchased, namely, (1) $\alpha_{s1}$-casein, (2) Na-caseinate, (3) soybean 11S globulin, (4) soybean 7S globulin, (5) soybean protein isolate "Ajipron S-2" (manufactured by Ajinomoto Co., Inc.), (6) water-extracted soybean protein, (7) acid-precipitated soybean protein, (8) soybean protein particles, (9) soybean protein micelles and (10) gelatin in 0.02 U per 1 mg of protein followed by shake incubation at 55° C. for an hour. After allowing to stand at room temperature, test tubes with samples were turned upside down, whereby gelation was determined by noting whether the samples drifted down or not. The results are shown in Table 6.

2) Rabbit myosin was prepared as follows for use as a substrate for BTGase.

Following the method of Perry (Perry, S. V. (1955), Methods in Enzymology, vol. 2, pp. 582–588, Academic Press, New York), myosin was extracted from 25 g of rabbit skeletal muscle at 0° C. for 30 minutes in a 3-fold amount of 0.45M KCl, 5 mM ATP-MgCl$_2$ and 50 mM phosphate buffer (pH 6) and subsequently collected by dilution precipitation; myosin was dialyzed against 0.5M KCl and 20 mM Tris-maleate (pH 7.5) solution and centrifuged at $10^5 \times g$ for 60 minutes, and the supernatant was used as purified myosin. The concentration of protein was 1.5%. BTGase was added to the myosin under the same conditions as under 1) above to examine gelation ability. The results are shown in Table 6.

3) Prawn myosin was prepared as follows for use as a substrate for BTGase.

The shell of a fresh (live) prawn (body length of about 5 cm) was peeled off and the prawn flection muscle was taken out. After mincing, the mince was washed with ice water and homogenized under cooling in the presence of 0.1 mM DTT and 0.1 mM PMSF. By centrifugation, actomyosin was extracted and separated therefrom. By further ultracentrifugation at $10^5 \times g$ for 60 minutes, actin was removed to give a myosin-rich fraction. Further dilution precipitation and ultracentrifugation were repeated to give purified prawn myosin. It was found that this purified myosin was modified myosin because it had no Ca-ATPase activity and lost the ability to bind to actin. To 5 ml of this modified prawn myosin solution having a protein concentration of 3.6% (buffer: 0.5M KCl, 5 mM $CaCl_2$, 25 mM Tris-HCl (pH 7.5) and 5 mM DTT) were added 3.6 units of BTGase. By immersing in a water bath at 35° C., the reaction was initiated and carried out for 35 minutes at maximum.

The foregoing experimental results of gelation ability are summarized in Table 6.

For purposes of comparison, the results of gelation ability test with MTGase are also shown. The amount of MTGase added was 0.1 U per 1 mg of substrate protein.

TABLE 6

| Gelation of BTGases of Various Proteins (test tube inversion method) | | | |
|---|---|---|---|
| Protein Foodstuff | Concentration (%) | BTGase | MTGase |
| $\alpha_{s1}$-Casein | 5 | ○ | ○ |
| | 10 | ○ | ○ |
| Na-Caseinate | 5 | ○ | Δ |
| | 10 | ○ | ○ |
| Soybean 11S globulin | 5 | ○ | Δ |
| | 10 | ○ | ○ |
| Soybean 7S globulin | 5 | ○ | x |
| | 10 | ○ | ○ |
| Ajipron S-2 | 5 | ○ | x |
| | 10 | ○ | ○ |
| Water-extracted soybean protein | 5 | ○ | x |
| | 10 | ○ | ○ |
| Acid-precipitated soybean protein | 5 | ○ | x |
| | 10 | ○ | ○ |
| Soybean protein particles | 5 | ○ | x |
| | 10 | ○ | Δ |
| Soybean protein micells | 5 | Δ | x |
| | 10 | ○ | Δ |
| Gelatin | 5 | ○ | x |
| | 10 | ○ | ○ |
| Rabbit myosin | 1.5 | ○ | ○ |
| Prawn myosin | 3.6 | ○ | ○ |

Notes:
○: gelled
Δ: weakly gelled
x: remained as solution
MTG was reacted at 37° C. for an hour.

Example 5

0.1M Tris-HCl buffer (pH 7.6) was added to gelatin (manufactured by Nitta Gelatin Co., Ltd.) so as to form 5.10 wt. % solution. Gelatin was completely dissolved at 60° C. for 3 minutes and the same BTGase as that of Example 4 was added to the solution in 0.02 U/mg protein. After thoroughly mixing, the mixture was reacted at 37° C. for an hour and then heated in a boiling water bath for 10 minutes. Immediately thereafter, the condition was observed.

For purposes of comparison, the system which was identically treated except for adding no BTGase was used as control. The results are shown in Table 7.

TABLE 7

| | −BTG | +BTG |
|---|---|---|
| 5% Gelatin | x | ○ |
| 10% Gelatin | x | ○ |

Notes:
x: complete solution
○: gelled condition (not dissolved even after heating)

Example 6

A silk protein aqueous solution was prepared as follows for use as a substrate for BTGase. To 100 ml of 9.3M lithium bromide (LiBr) solution was added 2.33 g of defatted silk yarn. When the mixture was stirred at 40° C. overnight, the silk yarn was solubilized. Suction filtration of the solution and dialysis to water were carried out to give a crude silk protein aqueous solution (approximately 2 wt. %). The same BTGase as used in Example 4 was previously charged in test tubes in final concentrations of 0.01 U, 0.02 U and 0.04 U/mg protein, respectively, and the silk protein aqueous solution was gently added thereto in order to avoid gelation due to shaking. For control, a BTGase-free solution was also prepared. After allowing each test tube to stand at room temperature overnight, the state of the sample in each test tube was observed to give the results shown in Table 8.

TABLE 8

| Sample | Condition |
|---|---|
| Silk protein aqueous solution − BTG | x |
| Silk protein aqueous solution + BTG (0.01 U/mg protein) | ○ |
| Silk protein aqueous solution + BTG (0.02 U/mg protein) | ○ |
| Silk protein aqueous solution + BTG (0.04 U/mg protein) | ○ |

Notes:
x: Fell down by inverting test tube. Transparent solution-like state.
○: Did not fall down even by inverting test tube. Turbid gel-like state.

Example 7

Commercially available milk (crude protein, 2.9%) was condensed to approximately 5-fold (crude protein, 14.5%) under reduced pressure. To 1 liter of the thus obtained condensed milk were added 2 units of BTGase shown in Example 4. The mixture was agitated to incubate at 55° C. for 30 minutes. The formed gel-like product was heated at 80° to 90° C. for 20 minutes to inactivate the remaining enzyme. It was then cooled to give a pudding-like gel foodstuff. A similar gel-like product could be obtained even by adding sugar thereto up to approximately 10%, if necessary.

Example 8

Commercially available milk (crude protein, 2.9%; oils and fats, 32.%; moisture content, 89%) was condensed to approximately 5-fold under reduced pressure to give condensed milk (approximately 10 liters). To the thus obtained condensed milk was added 100 ml of 30% glucono-delta-lactone solution. After rapidly mixing them, it was confirmed that the pH was 6.0 or greater. Then, 100 units of BTGase shown in Example 4 were added. The mixture was agitated and settled in an incubator at 45° C. for 45 minutes to cause gelation. Thereafter the gel was heated to 80° to 95° C. with caution so that the gel was not broken, whereby inactivation of BTGase and decomposition of glucono-delta-lactone to gluconic acid were carried out to adjust the pH of the gel to 4 to 5. After cooling, the card-like gel was cut into a square of approximately 8 cm and rendered a salt concentration of approximately 2% by the acid salt method. Starter of *Penicillium caseicolum* was inoculated thereon and ripened at 15° C. for 3 weeks at RH of 85% to give cheese.

In the case of using no glucono-delta-lactone, *Lactobacillus acidophillus* was added and after gelation by BTGase, fermentation was performed at 40° C. for 2 to 5 hours. Also in this case, similar cheese was obtained.

The cheese obtained by this process can be produced without using expensive calf rennet and physical properties thereof were considerably soft elasticity, resulting in good quality.

Example 9

Condensed milk (1 liter) of Example 8 was cooled to approximately 5° C. and a starter composed of *Streptococcus thermophillus* was added thereto and immediately mixed with each other. 1 unit of BTGase as used in Example 4 was added to the mixture. The system was settled in an incubator at 35° C. for an hour to cause gelation. Then, the gel temperature was raised to 50° C. followed by heating for 40 minutes. After an acid was formed by *S. thermophillus* and flavor was increased, the system was further heated at 75° to 85° C. to inactivate BTGase. Upon cooling, a yoghurt-like foodstuff having mild acid taste and excellent quality was obtained.

Example 10

Commercially available soybean milk (manufactured by Meiji Milk Products Co., Ltd., Sunglow Soybean Milk, crude protein, 3.1%) was condensed to approximately 2.5-fold under reduced pressure and cooled to 20° C. or lower to give condensed milk (crude protein, 7.75%). To 1 liter of the condensed milk were added 4 units of BTGase shown in Example 4. The mixture was charged in a plastic container. After the container was covered and sealed, it was heated on a hot water bath of 55° C. for 30 minutes to cause enzyme reaction and gelation. Thereafter, heating was performed using a high frequency dielectric heater (electronic oven, 2450 MHz, wavelength of 12 cm). Softer bean curd or tofu-like gel free from collapse of shape and having good quality was obtained as compared to silk-strained tofu or cotton-strained tofu.

Example 11

In approximately 20 kg of water was immersed 6.5 kg of whole soybeans, in which water was thoroughly absorbed at normal temperature overnight to swell the soybeans. While adding water thereto, the soybeans were ground with a crusher to obtain "go" or a soybean suspension. 25 kg of water was added thereto to dilute the go. A small quantity of a defoaming agent was added thereto and the mixture was transferred to a boiling vessel. Steam was blown into the vessel to heat it. It is preferred that heating conditions of elevating to 100° C. over 5 minutes and then keeping the temperature for 3 to 5 minutes be adopted. After boiling, tofu lees was removed with a tofu lees squeezer to give 30 kg of condensed soy milk (crude protein, 7.0%; oil, 8.1% and moisture content, 75%). To the soy milk were added 200 units of BTGase shown in Example 4 and the mixture was immediately packed in a casing tube (vinylidene chloride-made tube) followed by heating at 37° C. for 30 minutes. Then, the tube was transferred onto a hot water bath of 90° C. or more and heated (30 to 60 minutes). Tofu-like gel was obtained in running water.

Example 12

Kamaboko or steamed fish paste was prepared by way of experimentation, according to a recipe shown in Table 9. Physical properties were measured with a rheometer (manufactured by Fudo Chemical Co., Ltd.) and organoleptic evaluation (n=10) was performed. The addition amount of BTGase was 20 units per 1 g of dry fish paste. The enzyme reaction was carried out at 34° C. for 2 hours as in a seating step of BTGase-free control. After completion of the reaction, heating was performed at 85° C. for 30 minutes to make a product.

TABLE 9

|  | Control (%) | BTGase Added (%) |
| --- | --- | --- |
| Fish paste grade C | 66.9 | 66.9 |
| Potato starch | 6.7 | 6.7 |
| Sweet sake | 2.0 | 2.0 |
| Sugar | 2.0 | 2.0 |
| Table salt | 1.7 | 1.7 |
| MSG | 0.7 | 0.7 |
| Water | 20.0 | 19.3 |
| BTGase | 0 | 0.2 |

The results of the measurement of physical properties and the organoleptic evaluation are shown in Tables 10 and 11, respectively.

TABLE 10

|  | Breaking Strength (g) | Strain (%) |
| --- | --- | --- |
| Control (BTGase free) | 454 ± 50 | 44.3 ± 2.3 |
| BTGase | 804 ± 58 | 46.3 ± 1.3 |

TABLE 11

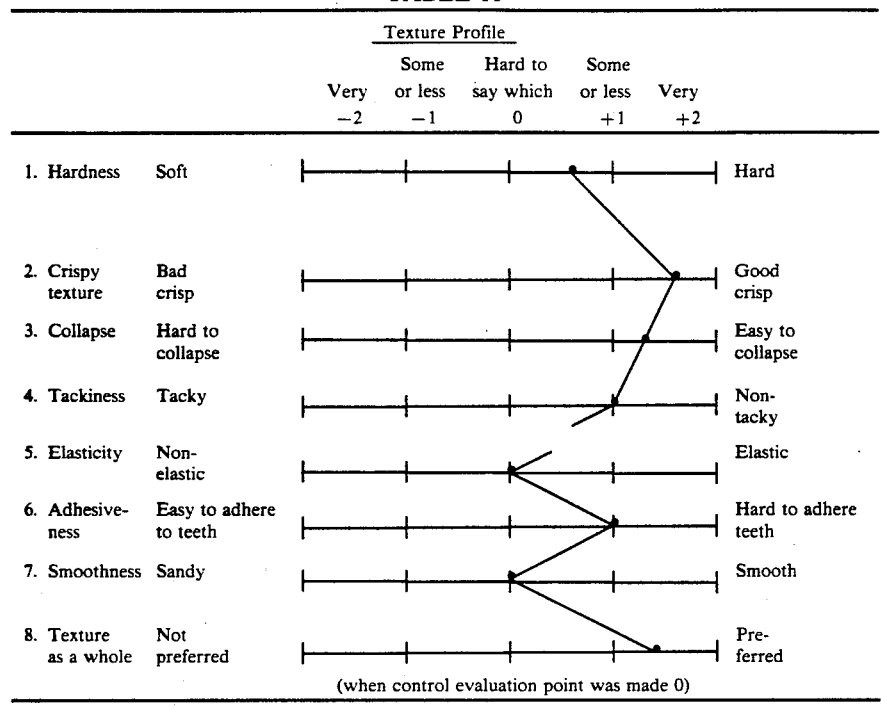

(when control evaluation point was made 0)

As described above, it was found that Kamaboko or fish paste which was prepared, by way of experiment, by adding BTGase thereto showed an increased breaking strength and provided a preferred texture, as compared to the control.

Example 13

Sausage was prepared by way of experimentation, according to a recipe shown in Table 12. Physical properties were measured with a rheometer (manufactured by Yamaden Co., Ltd.) and organoleptic evaluation (n=10) was performed. The amount of BTGase added was 1 unit per 1 g of dry pork. The enzyme reaction was carried out at 55° C. for 2 hours. After completion of the reaction, heating was performed at 80° C. for 30 minutes to make a product. As a control, BTGase-free product was used.

TABLE 12

|  | Control (%) | BTGase Added (%) |
|---|---|---|
| Pork shank | 68.4 | 68.4 |
| Table salt | 1.5 | 1.5 |
| Sodium nitrite | 0.02 | 0.02 |
| Na ascorbate | 0.06 | 0.06 |
| Sugar | 2.1 | 2.1 |
| MSG | 0.4 | 0.4 |
| White pepper | 0.3 | 0.3 |
| Water | 27.22 | 27.20 |
| BTGase | 0 | 0.02 |

The results of the measurement of physical properties and the organoleptic evaluation are shown in Tables 13 and 14, respectively.

TABLE 13

|  | Elasticity ($\times 10^5$ dyn.cm$^{-2}$) | Viscosity Coefficient ($\times 10^9$ dyn.sec.cm$^{-2}$) |
|---|---|---|
| Control | 4.73 | 1.48 |
| BTGase Added | 5.83 | 1.92 |

TABLE 14

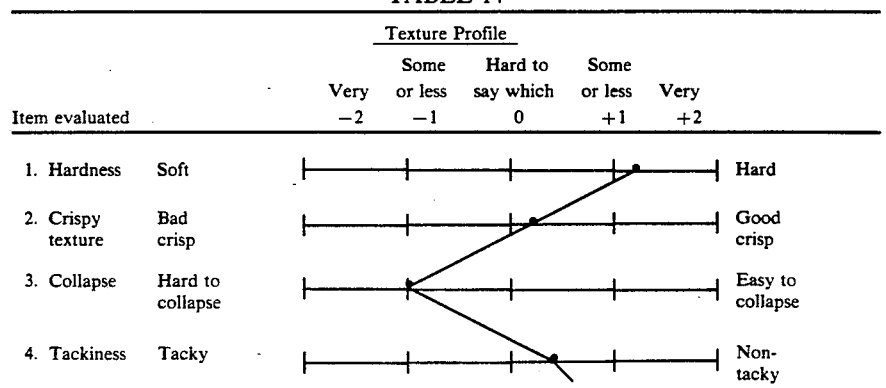

TABLE 14-continued

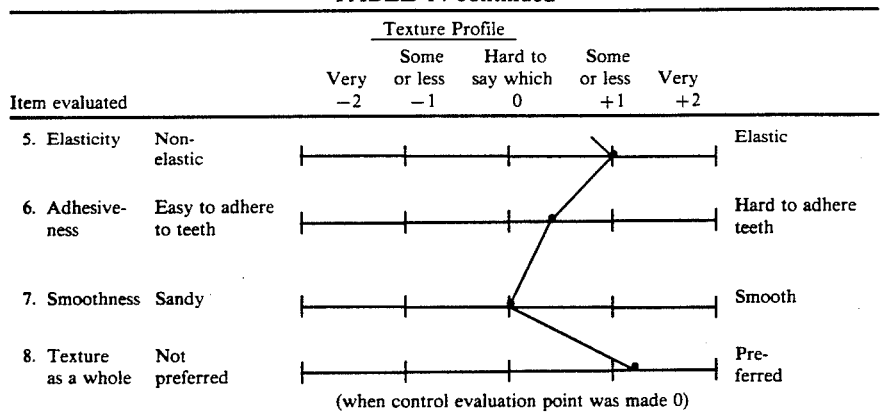

(when control evaluation point was made 0)

As described above, it was found that sausage which was prepared, by way of experimentation, by adding BTGase thereto provided a highly viscoelastic and preferable texture because of the gel forming ability of BTGase, as compared to the control.

Example 14

Whipping cream was prepared by way of experimentation, according to a recipe shown in Table 15 and a squeezing property was evaluated. The amount of BTGase added was 1 unit per 1 g of dry sodium caseinate. Whipping operation was performed using all purpose mixer (manufactured by San-Ei Seisakusho K.K.) at 7° to 9° C. As a control, BTGase-free product was used.

TABLE 15

|  | Control (%) | BTGase Added (%) |
| --- | --- | --- |
| Palm oil | 25.0 | 25.0 |
| Sodium caseinate | 5.0 | 5.0 |
| Monoglyceride | 0.3 | 0.3 |
| Water | 69.7 | 69.7 |
| BTGase | — | 0.005 |

Using each whipping cream, a flower pattern was drawn on a glass plate and the condition was observed. With the whipping cream with BTGase added, imitation flowers having sharp lines could be drawn.

Example 15

Ice cream was prepared by way of experimentation, according to a recipe shown in Table 16. Change in shape was observed when allowed to stand at room temperature and melt down resistance was evaluated. The amount of BTGase added was 25 units per 1 g of dry skim milk and the enzyme reaction was carried out at a sterilizing step (68° C., 30 minutes) of ice cream mix. After sterilizing, the ice cream mix was aged at 5° C. overnight and then frozen at an ice cream temperature of −2° to 4° C. using an ice freezer (manufactured by Mitsubishi Heavy Industries, Ltd.) up to overrun of 90%. After packing in a corn, it was hardened at −40° C. to make a product. As a control, ice cream prepared by way of experimentation in a similar manner except for adding no BTGase was used.

TABLE 16

|  | Control (%) | BTGase Added (%) |
| --- | --- | --- |
| Palm oil | 5.0 | 5.0 |

TABLE 16-continued

|  | Control (%) | BTGase Added (%) |
| --- | --- | --- |
| Skim milk | 8.0 | 8.0 |
| Sugar | 13.0 | 13.0 |
| Thick malt syrup | 6.0 | 6.0 |
| Gujar gum | 0.1 | 0.1 |
| Carrageenan | 0.1 | 0.1 |
| Locust bean gum | 0.1 | 0.1 |
| Monoglyceride | 0.3 | 0.3 |
| Vanilla essence | 0.1 | 0.1 |
| Water | 67.3 | 67.1 |
| BTGase | — | 0.2 |

The control collapsed in 15 minutes after allowing to stand at room temperature but the ice cream with BTGase added caused no collapse even after 30 minutes or longer and provided smooth touch to the tongue as in the control.

Example 16

A necessary amount of oxhide-derived atelo-collagen powders (manufactured by Kouken K.K.) were taken in a test tube and 2 ml of 0.1M Tris-HCl buffer (pH 7.5) was added thereto. After maintaining in a water bath at 55° C. for 15 minutes, the mixture was stirred to prepare 3 to 10% atelo-collagen solutions. Before the solutions of high concentration were gelled due to cooling, BTGase was added thereto in 0.05 U/mg protein followed by incubation at 55° C. for 60 minutes. As a control for the all samples, 10% atelo-collagen solution with no BTGase added was also incubated likewise. Immediately after completion of the incubation, the system was allowed to stand at room temperature for 60 minutes. Then the system was further kept in a water bath of 100° C. for 15 minutes and then the condition in the test tube was observed. The results are shown in Table 17.

TABLE 17

|  | Immediately After Completion of Incubation | After Allowing to Stand for 60 Minutes | After Heating at 100° C. |
| --- | --- | --- | --- |
| 3% Solution + BTGase | o | o | o |
| 5% Solution + BTGase | o | o | o |
| 10% Solution + BTGase | o | o | o |
| 10% Solution − BTGase | x | o | x |

Key:
o: gelled
x: not gelled

Example 17

Frozen fresh krill, 1 kg, (manufactured by Taiyo Fishery Co., Ltd.) was minced with a frozen cutter and, 30 g of table salt, 100 g of sorbitol (manufactured by Ajinomoto, Inc.), 50 g of Shin-Neriaji (manufactured by Ajinomoto, Inc.), 40 g of sweet sake and 50 g of potato starch were added thereto. Further, 200 units of BTGase dissolved in 300 ml of chilled water were added to the mixture followed by kneading with a cutter manufactured by Stephan Co., Ltd. for approximately 6 minutes. The temperature immediately after the kneading was controlled to 5° to 6° C. This krill paste was packed in a casing tube made of vinylidene chloride (manufactured by Kureha Chemical Industry Co., Ltd.). After incubating at 50° C. for an hour, it was heated in a boiling hot water bath for 25 hours. After heating, it was cooled by running water and physical properties thereof were then measured. Namely, the sample was cut into pieces having a thickness of 3 cm. Using a spherical plunger having a diameter of 7 mm, breaking strength was determined by measuring with a rheometer manufactured by Fudo Chemical Industry Co., Ltd. The results are shown in Table 18. As a control, a sample was prepared in a similar manner except for using BTGase denatured to inactivate by previously heating to high temperatures.

TABLE 18

| | Breaking Strength (g/cm²) |
|---|---|
| Control | 286 |
| BTGase Added | 442 |

That is, it was noted that Kamaboko or krill paste prepared by way of experimentation by adding BTGase thereto showed much higher breaking strength than the control obtained using the previously inactivated BTGase.

Example 18

Japanese noodle was prepared in a recipe shown in Table 19. Organoleptic evaluation (n=15) and measurement of physical properties were performed.

TABLE 19

| | Control (%) | BTGase Added (%) |
|---|---|---|
| Strong flour | 36.4 | 36.4 |
| Weak flour | 36.4 | 36.4 |
| Table salt | 0.5 | 0.5 |
| Water | 26.7 | 26.7 |
| BTGase | — | 0.04 |

The addition of BTGase was 1 U per 1 g of protein. After the enzyme reaction was carried out at room temperature for 2 hours, noodles were made. The organoleptic evaluation and the measurement of physical properties were conducted using Japanese noodles boiled for 12 minutes. The length of the noodle used for the measurement of physical properties was 7 cm. A tensile test was carried out using a rheometer (manufactured by Fudo Chemical Industry Co., Ltd.), and breaking strength and elongation to break were measured. The results are shown in Tables 20 and 21.

TABLE 20

Texture Profile
(evaluation point of the sample added with BTGase when the control was made 0)

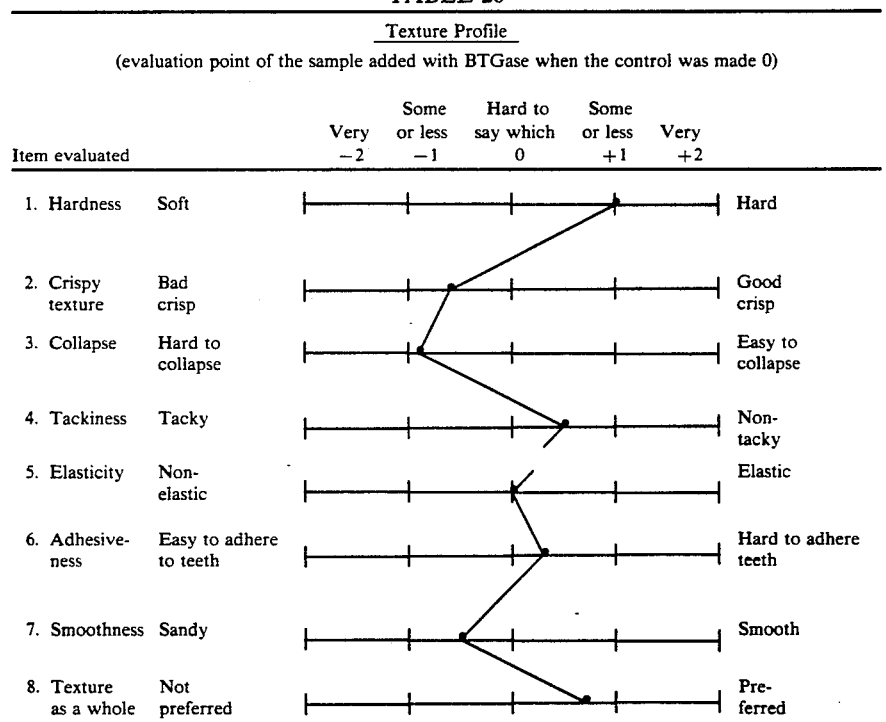

TABLE 21

| | Breaking Strength (g) | Elongation (%) |
|---|---|---|
| Control (BTGase free) | 706 ± 23 | 64 ± 5 |
| BTGase | 885 ± 48** | 51 ± 13 | n = 10  **Significant difference was noted with a significance level of 1%.

The results of the organoleptic evaluation were consistent with those of the measurement of physical properties, and it was found that by adding BTGase, cross-linking structure between gluten molecules was formed and noodles having a firm texture similar to special Japanese noodles of the someday district.

Example 19

Spaghetti was prepared according to a recipe shown in Table 22. Organoleptic evaluation (n=15) and measurement of physical properties were performed.

TABLE 22

|  | Control (%) | BTGase Added (%) |
| --- | --- | --- |
| Strong flour | 73.7 | 73.7 |
| Table salt | 0.6 | 0.6 |
| Water | 25.7 | 25.7 |
| BTGase | — | 0.04 |

The addition of BTGase was 1 U per 1 g of protein. After the enzyme reaction was carried out at room temperature for 2 hours, spaghetti was made with a pasta machine (manufactured by Lucky Coffee Maker Co., Ltd.). The organoleptic evaluation and the measurement of physical properties were conducted using spaghetti boiled for 5 minutes and 30 seconds. The length of the spaghetti used for the measurement of physical properties was 7 cm. A tensile test was carried out using a rheometer (manufactured by Fudo Chemical Industry Co., Ltd.) and, breaking strength and elongation to break were measured. The results are shown in Tables 23 and 24.

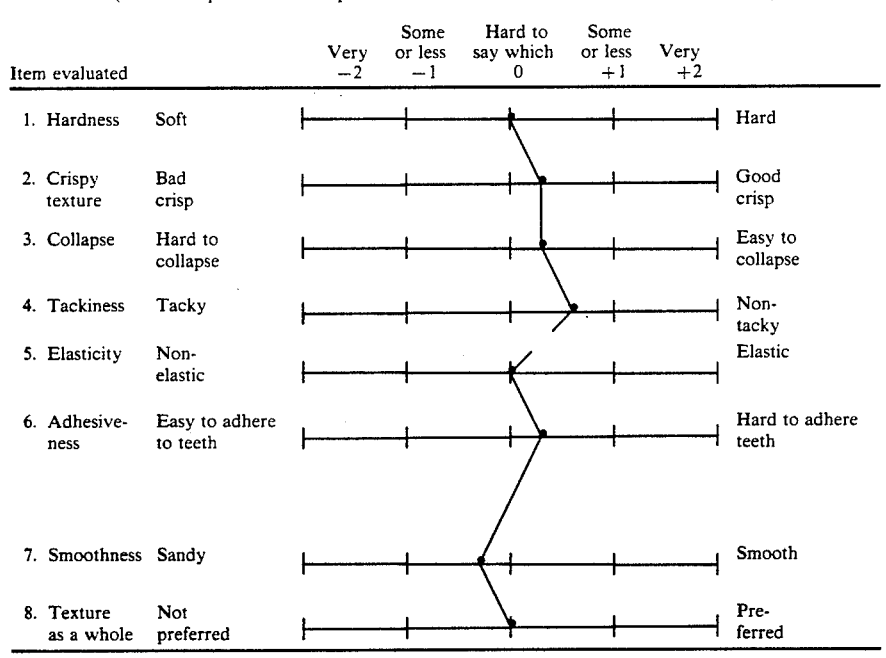

TABLE 23 — Texture Profile (evaluation point of the sample added with BTGase when the control was made 0)

TABLE 24

|  | Breaking Strength (g) | Elongation (%) |
| --- | --- | --- |
| Control | 29 ± 2 | 77 ± 7 |
| BTGase | 27 ± 1 | 54 ± 9** | n = 10 **Significant difference was noted with significance level of 1%.

Even though BTGase acted on spaghetti, no significant change occurred in the texture as shown in Table 23 but powders mixed at the preparation step were light and operability was greatly improved in that feeding into a screw was smooth and heat generation in a cylinder was minimized, etc.

Effects of the Invention

Microorganism-derived BTGase of the present invention can be supplied at low cost and can be easily purified and therefore, is highly practical.

It is also advantageous that by the use of a BTGase according to this invention, gelation products having excellent quality can be produced using a very low enzyme (BTGase) concentration and in a very low substrate concentration in the absence of calcium or even in the presence of calcium.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States:

1. A transglutaminase which catalyzes an acyl transfer reaction of a γ-carboxyamide group of a glutamine residue in a peptide or protein chain independently of $Ca^{2+}$.

2. The transglutaminase of claim 1, obtained from a microorganism of the genus Streptoverticillium.

3. A process for producing a transglutaminase, which comprises culturing a microorganism of a strain belonging to the genus Streptoverticillium capable of producing a transglutaminase which catalyzes an acyl transfer reaction of a γ-carboxyamide group of a glutamine residue in a peptide or protein chain independently of $Ca^{2+}$, and harvesting said transglutaminase from the culture.

4. A process for producing a protein gelation product, which comprises contacting a protein-containing solution or slurry having a protein concentration of at least 1.0 wt. % with a transglutaminase which catalyzes an acyl transfer reaction of a γ-carboxyamide group of a glutamine residue in a peptide or protein chain independently of $Ca^{3+}$ for a time sufficient to result in gelation of said solution or slurry.

5. A process as claimed in claim 4 wherein 0.01 to 2000 units of said transglutaminase are incorporated per 1.0 g of the protein contained in said solution or slurry.

6. The process of claim 4, wherein said transglutaminase is obtained from the genus Streptoverticillium.

* * * * *